(12) United States Patent
Ostrovsky et al.

(10) Patent No.: US 9,675,343 B2
(45) Date of Patent: Jun. 13, 2017

(54) WIRE COIL TISSUE FIXATION DEVICE

(71) Applicant: Boston Scientific Scimed, Inc., Maple Grove, MN (US)

(72) Inventors: Isaac Ostrovsky, Wellesley, MA (US); Michael F Weiser, Groton, MA (US); Timothy P Harrah, Cambridge, MA (US); Ty Fairneny, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 240 days.

(21) Appl. No.: 14/453,112

(22) Filed: Aug. 6, 2014

(65) Prior Publication Data

US 2015/0045612 A1 Feb. 12, 2015

Related U.S. Application Data

(60) Provisional application No. 61/864,990, filed on Aug. 12, 2013.

(51) Int. Cl.
| | |
|---|---|
| *A61F 2/00* | (2006.01) |
| *A61F 13/00* | (2006.01) |
| *A61B 17/064* | (2006.01) |
| *A61B 17/068* | (2006.01) |

(52) U.S. Cl.
CPC .......... *A61B 17/064* (2013.01); *A61B 17/068* (2013.01); *A61B 2017/0649* (2013.01); *A61F 2/0063* (2013.01)

(58) Field of Classification Search
CPC ................ A61B 17/064; A61B 17/068; A61B 2017/0649; A61F 2/0063

USPC ........ 600/37, 29, 30; 128/897–899; 606/158
See application file for complete search history.

(56) References Cited

U.S. PATENT DOCUMENTS

| | | | | |
|---|---|---|---|---|
| 6,663,633 | B1 * | 12/2003 | Pierson, III ........ | A61B 17/0469 606/148 |
| 6,884,248 | B2 | 4/2005 | Bolduc et al. | |
| 7,077,850 | B2 | 7/2006 | Kortenbach et al. | |
| 7,811,295 | B2 | 10/2010 | Kortenbach et al. | |
| 2002/0013605 | A1 * | 1/2002 | Bolduc ............... | A61B 17/064 606/213 |
| 2003/0009441 | A1 * | 1/2003 | Holsten ............... | A61B 17/068 |
| 2004/0127916 | A1 * | 7/2004 | Bolduc ............... | A61B 17/064 606/151 |

(Continued)

*Primary Examiner* — Navin Natnithithadha
*Assistant Examiner* — Sunita Reddy
(74) *Attorney, Agent, or Firm* — Brake Hughes Bellermann LLP

(57) ABSTRACT

In one embodiment, a medical device includes an elongate member, a fixation device and a driving member. The elongate member defines a lumen and includes a proximal end and a distal end. The distal end of the elongate member has an opening. The fixation device is at least partially disposed within the elongate member and includes a tissue piercing portion at a distal end of the fixation device. The driving member is at least partially disposed within the elongate member and is configured to move the fixation device from a position within the lumen to a location outside of the lumen through the opening. The opening at the distal end of the elongate member is angled to insert the fixation device in a tissue of a patient at an angle to a plane of the tissue of the patient to fasten a bodily implant to the tissue.

20 Claims, 13 Drawing Sheets

(56) References Cited

U.S. PATENT DOCUMENTS

| | | | |
|---|---|---|---|
| 2005/0187613 A1* | 8/2005 | Bolduc | A61B 17/064 623/1.23 |
| 2006/0100640 A1* | 5/2006 | Bolduc | A61B 17/00234 606/108 |
| 2010/0001038 A1* | 1/2010 | Levin | A61B 17/064 227/179.1 |
| 2012/0053598 A1* | 3/2012 | Chin | A61B 17/0469 606/139 |
| 2012/0083806 A1* | 4/2012 | Goertzen | A61B 17/0401 606/151 |
| 2013/0006049 A1* | 1/2013 | Alexander | A61F 2/0045 600/37 |
| 2014/0257032 A1* | 9/2014 | Hacker | A61F 2/0045 600/37 |

* cited by examiner

WIRE COIL TISSUE FIXATION DEVICE

CROSS-REFERENCE TO RELATED APPLICATION

This application is a Nonprovisional of, and claims priority to, U.S. Patent Application No. 61/864,990, filed on Aug. 12, 2013, entitled "WIRE COIL TISSUE FIXATION DEVICE", which is incorporated by reference herein in its entirety.

TECHNICAL FIELD

This disclosure relates generally to medical devices and more particularly to medical devices that include fixation devices or tissue fasteners.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures include placing a support member or implant into the body of the patient such that the support member or implant provides support to a portion of the body of the patient. Specifically, in some medical procedures, the support member or implant may be fixed or coupled to the body of the patient at various locations within the body of the patient and a support portion of the support member or implant may be placed beneath the portion of the body to be supported. For instance, a patch of prosthetic material, such as a mesh material, may be attached to a layer (e.g., a thin layer) of tissues in the body of the patient such as a wall of an organ, for example, the vaginal wall. In some cases, a second portion of the mesh material may be attached to a layer of muscle or ligament on top of a bone such as, for example, the sacrum.

In some known medical procedures, fixation devices are used to fix or couple portions of the support member to portions of the body of the patient. A need exists for fixation devices that effectively retain a support member in place within a body of a patient and control a depth of penetration of the devices. A need also exists for a tool for effectively placing such fixation devices inside the body of the patient.

SUMMARY

In one general aspect, a medical device includes an elongate member, a fixation device and a driving member. The elongate member defines a lumen and includes a proximal end and a distal end. The distal end of the elongate member has an opening. The fixation device is at least partially disposed within the elongate member and includes a tissue piercing portion at a distal end of the fixation device. The driving member is at least partially disposed within the elongate member and is configured to move the fixation device from a position within the lumen to a location outside of the lumen through the opening. The opening at the distal end of the elongate member is angled to insert the fixation device in a tissue of a patient at an angle to a plane of the tissue of the patient to fasten a bodily implant to the tissue.

In another general aspect, a medical device includes an elongate member, a coil-shaped fastener and a driving member. The elongate member defines a lumen and includes a proximal end and a distal end. The distal end has an angled portion and an opening. The coil-shaped fastener is at least partially disposed within the elongate member and the coil-shaped fastener has an outside diameter. The driving member is at least partially disposed within the elongate member. The driving member is configured to move the coil-shaped fastener from a position within the lumen to a location outside of the lumen through the angled portion and the opening at the distal end of the elongate member and to insert the coil-shaped fastener in a tissue of a patient to fasten a bodily implant to the tissue.

In another general aspect, a method of placing a coil-shaped fastener within a body of a patient includes 1) inserting a medical device within the body of the patient, the medical device includes an elongate member defining a lumen, the elongate member having a distal end and an angled opening at the distal end and 2) moving the coil-shaped fastener from a position within the elongate member to a location outside of the elongate member through the angled opening at the distal end.

DETAILED DESCRIPTION

Figure 1:
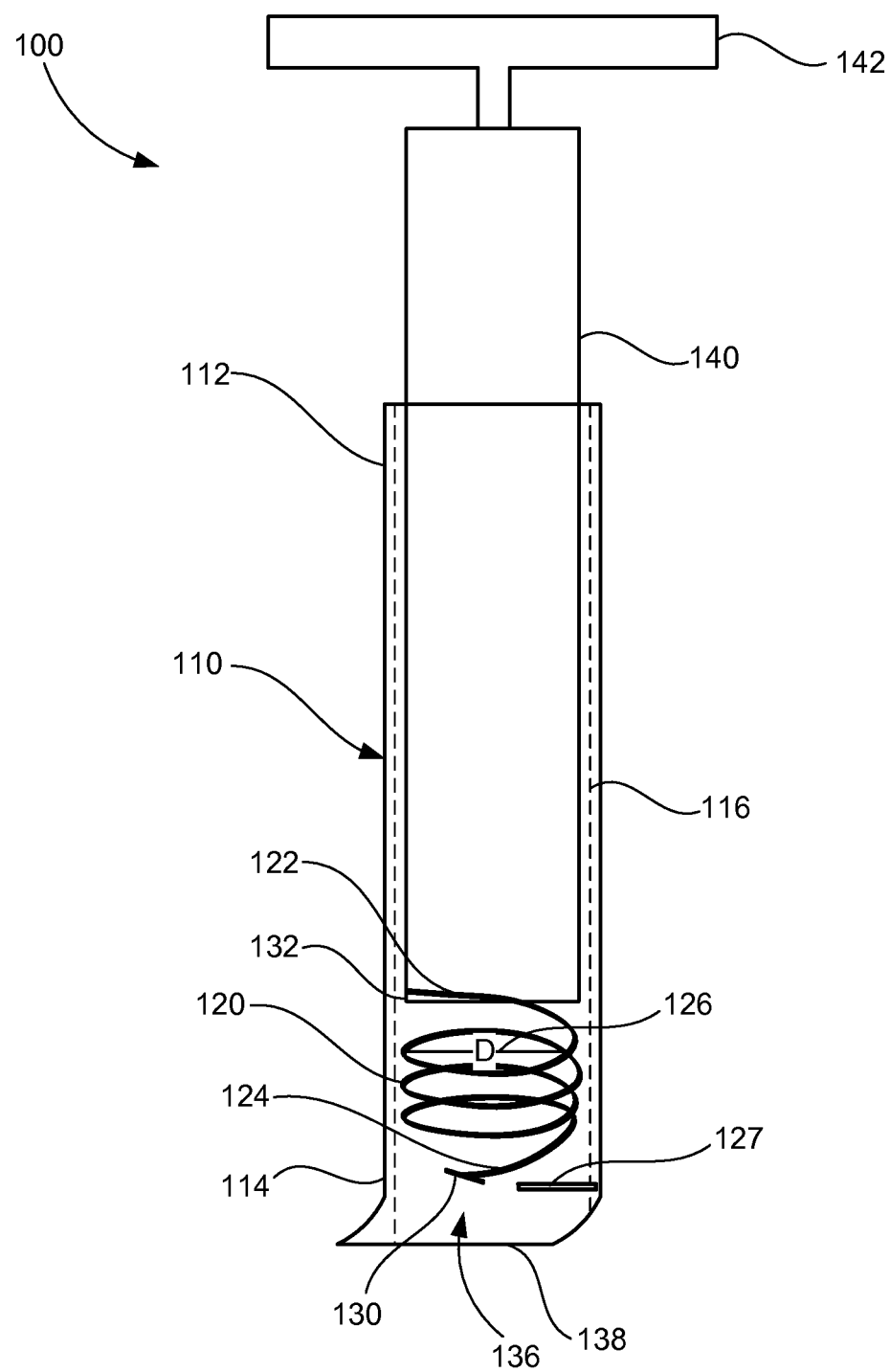
FIG. 1 is a schematic illustration of an apparatus according to an embodiment of the invention.

The devices and methods described herein are generally directed to procedures for placing implants within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured or coupled to a vaginal wall.

In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved.

Various fixation devices or wire coil fixation devices or coil-shaped fasteners, delivery devices, and methods are described for delivering and securing an implant within the body of the patient. The implants, fixation devices, delivery devices, and procedures described herein may be used in a female patient or a male patient.

An implant according to an embodiment of the invention can be implanted, for example, through an abdominal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision. For example, a procedure may include an abdominal incision to secure or couple an implant to a vaginal wall.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

FIG. 1 is a schematic illustration of an apparatus or medical device 100 according to an embodiment of the invention. The apparatus or medical device 100 includes an elongate member 110, a fixation device 120 and a driving member 140.

The apparatus 100 is configured to be inserted into a body of a patient such that at least a portion of the apparatus 100 is disposed within the body of the patient. As will be discussed in more detail below, the apparatus is configured to be placed adjacent a desired coupling or fixation location within the body.

The elongate member 110 includes a first end portion 112 (or proximal end) and a second end portion 114 (or a distal end). The elongate member 110 defines a lumen 116 (shown in dashed lines in FIG. 1). In some embodiments, the lumen 116 extends from the first end portion 112 to the second end portion 114. In some embodiments, the elongate member 110 defines an opening at the first end portion 112 and an opening at the second end portion 114 and the lumen 116 extends between the opening at the first end portion 112 and the opening at the second end portion 114. In other embodiments, the lumen only extends through a portion of the length of the elongate member 110. The lumen 116 is configured to receive and house various components of the apparatus 100 as will be described in detail below.

Figure 2:
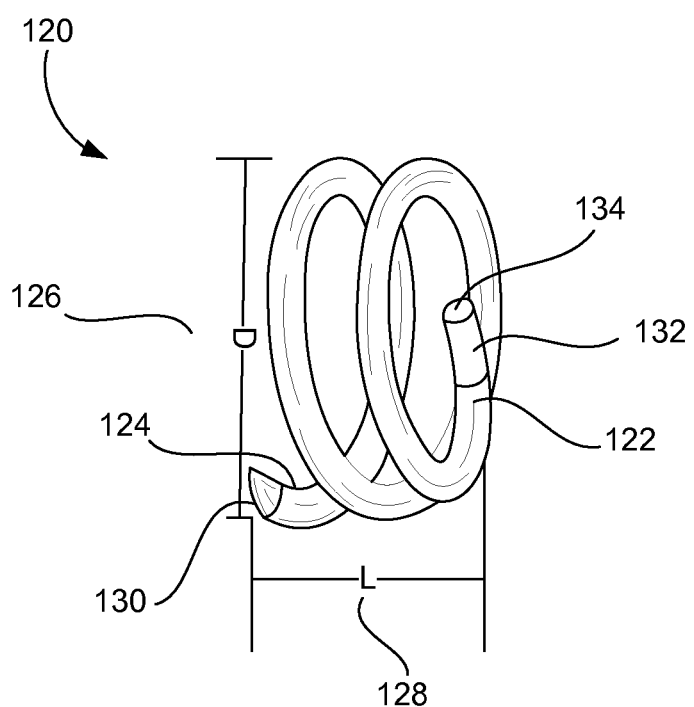
FIG. 2 is a perspective view of a fixation device according to an embodiment of the invention.

Referring also to FIG. 2, the fixation device 120 is configured to be placed within a body of a patient and to be fixedly coupled to a portion of the body of the patient. The terms fastener, fastener device and fixation device are used interchangeably throughout this document to mean the same thing. For example, in some embodiments, the fixation device 120 is configured to engage a bodily implant and be coupled to body tissue within the body of the patient to fixedly couple the implant to the body tissue.

In some embodiments, the fixation device 120 is a coil-shaped fastener (or wire coil or wire coil fixation device or coil-shaped fixation device). The fixation device 120 includes a first end 122 and a second end 124. The fixation device 120 includes multiple turns of a wire that form a coil-shaped wire between the first end 122 and the second end 124. The turns of the coil may form an outside diameter (D) 126. The diameter 126 may be uniform for each turn of the fixation device 120. In some embodiments, the diameter 126 may not be uniform for each turn of the fixation device 120, where some turns of the coil may have a smaller diameter than the outside diameter 126. In those embodiments, the diameter 126 may define the largest diameter for all of the turns of the coil.

A distance between the first end 122 and the second end 124 may define a length (L) 128 of the coil 120. The length 128 may be the length of the fixation device 120 when the fixation device 120 is in a coil configuration. Said another way, the length 128 is not the length of the wire stretched straight from end to end. Instead, the length 128 is measured from the first 122 to the second end 124 along an axis through the fixation device 120 when the wire is shaped in a coil.

In some embodiments, the fixation device 120 may have variable pitch along its length. In some embodiments, the fixation device 120 may have a variable diameter along its length.

The fixation device 120 is configured to enter a tissue of a patient to a specified depth. In some embodiments, the diameter 126 may define the maximum depth of penetration into the tissue of the patient. For example, when the fixation device 120 is inserted into the tissue in a plane parallel to the tissue (as shown in more detail in figures below), the diameter 126 may define the maximum depth of penetration. In this manner, a delivery of the fixation device 120 in a plane parallel to the tissue is configured to control the depth of penetration into the tissue of the patient, where the tissue may be soft tissue or hard tissue. The fixation device 120 may be prevented from penetrating the tissue more than the maximum depth as defined by the diameter 126.

In other example embodiments, a distance less than the length 128 may define the depth of penetration of the fixation device 120. For example, when the fixation device 120 is inserted into the tissue at an angle (as shown in more details in figures below), a distance less than the length 128 may define the maximum depth of penetration. In this manner, a delivery of the fixation device 120 at an angle to the plane of the tissue of the patient is configured to control the depth of penetration into the tissue, where the tissue may be soft tissue or hard tissue. The fixation device 120 may be prevented from penetrating the tissue more than the maximum depth as defined by a distance less than the length 128.

The cross-sectional profile of the wire may be of any geometry including round, square, rectangular, triangular, D-shaped, C-shaped and so forth. In particular, a rectangular profile can be found in a flat ribbon-like wire. Such flat wire may have a lower profile than other types of wire, which may be more desirable depending on the tissue and procedure.

In some embodiments, the fixation device 120 includes at least one tissue piercing portion 130. The tissue piercing portion 130 is configured to pierce or be inserted into bodily tissue. In one embodiment, the tissue piercing portion may be at the second end 124. The tissue piercing portion 130 of the coil may taper to a sharp point at the second end 124.

In some embodiments, the fixation device 120 includes a lever portion 132. The lever portion 132 is configured to provide a point of contact for the driving member 140 to drive the fixation device 120 into a tissue of a patient. The lever portion 132 may include flat portion 134 on the end of the lever portion 132. The flat portion 134 may provide the point of contact for the driving member 140 to drive the fixation device 120. In other embodiments, the lever portion 132 may include a thicker portion of wire compared to the remaining portion of the wire for the fixation device 120.

In one embodiment, the fixation devices 120 may be made of bio-compatible metal materials such as titanium, nitinol, elgiloy or stainless steel. Other bio-compatible metal materials may be used. The fixation devices 120 made of metal may be used in procedures where the bodily tissue is hard tissue such as sacrum, where a thin layer of tough ligament covers the bone. In some embodiments, materials include ceramics or biologics (e.g., collagen, fibrin, elastin, extracellular matrix, etc.) In some embodiments, the fixation devices 120 comprise more than one material. In some embodiments, the fixation devices 120 comprise a biodegradable material. In some embodiments, the fixation devices 120 comprise at least one biodegradable material and at least one non-biodegradable material. The fixation devices 120 may be fully or partially biodegradable. The fixation devices 120 may be made of metal, polymers, biologics or a combination of materials.

In some embodiments, the fixation devices 120 may be designed with the least amount of material necessary to function in order to have the least amount of irritation on bodily tissues when implanted. In some embodiments, the least amount of material may include one or more of the materials described above.

In some embodiments, the fixation devices 120 may become more flexible due to partial biodegradation, response to body heat, time or based on other triggers.

In some embodiments, the fixation devices 120 may comprise one or more coatings, coverings or other materials to improve the interaction with the bodily tissue at the implantation site. A coating or covering may keep the fixation device stiff for delivery and biodegrade after delivery to allow more in situ flexibility. In some embodiments, the entire fixation device 120 may be coated with one or more such coatings or other materials. In some embodiments, a portion of the fixation device 120 may be coated with one or more such coatings or other materials. In some embodiments the fixation device includes pores throughout to promote tissue ingrowth and assist in securing the device. In some embodiments, the fixation device has surface features such as bumps or grooves that facilitate the ingrowth of tissue into the device.

In the illustrated embodiment, the apparatus 100 includes an opening 136 at a distal end of the elongate member 110. The opening 136 is a point on the apparatus 100 where the fixation device 120 is pushed from a position within the elongate member 110 to a position outside of the elongate member 110. The opening 136 may be beveled or angled 138. The opening 136 may be beveled or angled to enable the fixation device 120 to be inserted into the tissue of a patient at an angle to a plane of the tissue of the patient. The degree of the angle of the opening 136 may determine the angle that the fixation device 120 will be inserted into the tissue. In this manner, the fixation device 120 is inserted into the tissue at a determined angle to control the depth of penetration of the fixation device 120 into the tissue.

In some embodiments, the angle of the opening 136 may be fixed. In this manner, the fixation device 120 is inserted into the tissue at an angle determined by the fixed angle of the opening 136. For instance, the fixation device 120 may be inserted into the tissue at an angle corresponding to the fixed angle of the opening 136. For example, the angle of the opening may be fixed at an angle to enable the fixation device 120 to be inserted parallel to the plane of the patient to fasten a bodily implant to the tissue. In another example, the angle of the opening may be fixed at an angle to enable the fixation device 120 to be inserted at an oblique angle to the plane of the tissue of the patient to fasten the bodily implant to the tissue.

In other embodiments, the angle of the opening 136 may be adjustable. In this manner, the fixation device 120 is inserted into the tissue at an angle determined by the adjustable angle of the opening 136. For instance, the fixation device 120 may be inserted into the tissue at an angle corresponding to the adjustable angle of the opening 136. For example, the angle of the opening may be adjustable to an angle to enable the fixation device 120 to be inserted parallel to the plane of the patient to fasten a bodily implant to the tissue. In another example, the angle of the opening may be adjustable to an angle to enable the fixation device 120 to be inserted at an oblique angle to the plane of the tissue of the patient to fasten the bodily implant to the tissue.

In the illustrated embodiment of FIG. 1, the apparatus 100 includes a driving member 140. The driving member 140 also may be referred to interchangeably as a pusher throughout this document. The driving member 140 is configured to be disposed within the lumen 116 defined by the elongate member 110. For example, in some embodiments, the driving member 140 is configured to be disposed within the lumen 116 such that a portion of the driving member 140 is disposed within the lumen 116 and a portion of the driving member 140 is disposed outside of the lumen 116.

The driving member 140 is configured to move from a first location to a second location with respect to the elongate member 110. For example, in some embodiments, the driving member 140 is configured to move from a first location within the lumen 116 to a second location within the lumen 116 different than the first location. The driving member 140 is configured to contact the fixation device 120 while the fixation device 120 is disposed within the elongate member 110 and force the fixation device 120 out of the elongate member 110. For example, in some embodiments, when the driving member 140 is at its first position within the lumen 116, the driving member 140 does not contact the fixation device 120. As the driving member 140 is moved from its first position to its second position, the driving member 140 contacts the fixation device 120 and moves the fixation device 120 within the elongate member 110. In some embodiments, the driving member 140 is configured to expel or push the fixation device 120 to a location outside of the elongate member 110 when the driving member 140 is in its second position. The driving member 140 is configured to engage the fixation device 120 and to drive the fixation device 120 to a position outside of the elongate member 110 and into the tissue of the patient at the desired angle and to the desired depth of penetration into the tissue.

In some embodiments, the driving member 140 contacts the fixation device 120 at the lever portion 134. The driving member 140 engages the lever portion 134 and moves the fastener through the elongate member 110 and drives the fixation device 120 into the tissue of the patient. In some embodiments, the coil-shape of the fixation device 120 causes the fixation device 120 to rotate in the tissue as the fastener is driven or pushed by the driving member 140. In other embodiments, the driving member 140 may impart a rotational motion to the fixation device 120 that causes the fixation device 120 to rotate in the tissue of the patient. In some embodiments, portions of the fixation device are linear rather than coiled. In some embodiments, lever portion 134 is located on a linear portion of the fixation device.

In some embodiments, the apparatus 100 may include a handle 142. The handle 142 is connected or attached to or a part of the driving member 140. The handle 142 may be configured to provide a holding or gripping point for the driving member 140 for a person using the apparatus 100. In some embodiments, the handle 142 may be configured to impart a rotational motion to the driving member 140, which imparts the rotational motion to the fixation device 120.

In some embodiments, the elongate member 110 is configured to house or receive multiple coil-shaped fasteners 120. In some embodiments, the fasteners 120 may be disposed serially or end to end within the elongate member 110. In such embodiments, the driving member 140 may be configured to contact and move one of the fasteners 120, which may in turn be configured to contact and move the other of the tacks.

In some embodiments, the elongate member 110 is configured to house a single continuous wire having a coil-shape. The apparatus 100 may be configured to separate or break the single continuous wire into multiple coil-shaped fasteners 120, where the fasteners 120 have a first end 122 and a second end 124 with a tissue piercing portion 130 at the second end 124. The apparatus 100 may include a cutting member 127 that is configured to separate the coil at a desired location. In some embodiments, the cutting member 127 may separate or break the coil at a desired location(s) by cutting the coil. In other embodiments, a cutting implement that is separate from the apparatus 100 may be used to break the coil at a desired location. In some embodiments, the wire is predisposed to break at certain points along its length to create discrete anchors. For example, there may be notches cut into wire. In some embodiments notches or other features enabling breakage are located periodically along the wire to permit discrete anchors to be formed of any length necessary or desired.

The single continuous wire having a coil-shape enables a user of the apparatus 100 to use fasteners 120 having different lengths 128. In use, the apparatus 100 may be used to insert a portion of the single continuous wire into tissue of a patient at a desired angle and length to achieve a desired depth of penetration. Then, a cutting member 127 or a cutting implement may be used to trim or cut the coil-shaped fastener. The apparatus 100 may again be used to insert another portion of the single continuous wire into the tissue of the patient, for example, at another location in the tissue. The other portion of the single continuous wire may be at a same angle and length or may be at a different angle and length to achieve a different depth of penetration. The cutting member 127 or the cutting implement may be used to trim or cut the coil-shaped fastener for the other section of the continuous wire coil.

In use, a fixation device 120 may be disposed within the elongate member 110. The fixation device 120 may be disposed within the lumen 116 defined by the elongate member 110. The elongate member 110 includes an opening 136 at the second end 114 (or distal end) of the elongate member 110. The opening 136 may be angled or beveled 138 to facilitate the insertion of the fixation device 120 at a desired angle and, correspondingly, a desired depth of penetration. The apparatus 100 may then be inserted into a body of a patient. For example, in some implementations, the apparatus 100 may be inserted into a body of a patient through an abdominal incision. In other implementations, the apparatus may be inserted into a body of a patient through a vaginal or other bodily incision. An end portion, such as the second end portion 114 (a distal end portion) of the elongate member 110 may be disposed adjacent to the bodily tissue into which the fixation device 120 is to be inserted. In some embodiments, a bodily implant, such as a mesh type bodily implant or a lead, may be disposed between the second end portion 114 of the elongate member 110 and the tissue.

The driving member 140 may then be moved with respect to the elongate member 110 within the lumen 116 defined by the elongate member 110. For example, the driving member 140 may be moved from a first position to a second position. As the driving member 140 is moved from its first position or location within the lumen 116 to its second position or location within the lumen 116, the driving member 140 contacts and moves the fixation device 120 from a location within the elongate member 110 a location outside of the elongate member 110 at an angle that may be determined by the angle of the opening 136. The driving member 140 may impart a rotational movement to the fixation device 120.

In some embodiments, as the fixation device 120 is moved to a location or position outside of the elongate member 110, the fixation device 120 will pierce the bodily implant and the desired tissue. As the fixation device 120 moves along the elongate member 110 through the opening 136 to a location outside of the elongate member 110, the fixation device 120 may be angled by the opening 136 so as to enter the desired tissue at an angle. Additionally, once the fixation device 120 is disposed outside of the elongate member 110 (and away from the elongate member 110), the fixation device 120 may penetrate the tissue to a depth defined by a diameter 126 of the fixation device 120 or defined by a distance that is smaller than the length 128 of the fixation device 120. Accordingly, the fixation device 120 will be embedded within the bodily tissue and the rotational movement of the coil-shape will grasp or secure a portion of the bodily tissue to fixedly couple the fixation device 120 (and the bodily implant) to the bodily tissue. In some embodiments, the fixation device 120 secures the bodily implant at multiple points of fixation in multiple different planes, as illustrated and described in more detail below.

In some embodiments, the medical device includes a second coil-shaped fastener. In such embodiments, the medical device may then be moved to another location within the body (and disposed adjacent different or another portion of bodily tissue). The second coil-shaped fastener may then be inserted to such portion of bodily tissue.

In some embodiments, the fixation device may be a straight wire within the medical device that is to deliver the fixation device. The wire may be formed into a coil at insertion as it exits the delivery device. In some embodiments, the fixation device may be coiled within the delivery device and then exit with a different pitch, angle and/or diameter.

In some embodiments, the medical device may include a piercing tip (e.g., a needle at a distal end of the device or a sharp ramp at the distal end of the device) and the fixation device may include a less sharp or even a blunt end (e.g., a flat or rounded end).

In some embodiments, a vacuum may be used to hold a seal between the medical device and tissue while delivering the fixation device.

Figure 3:
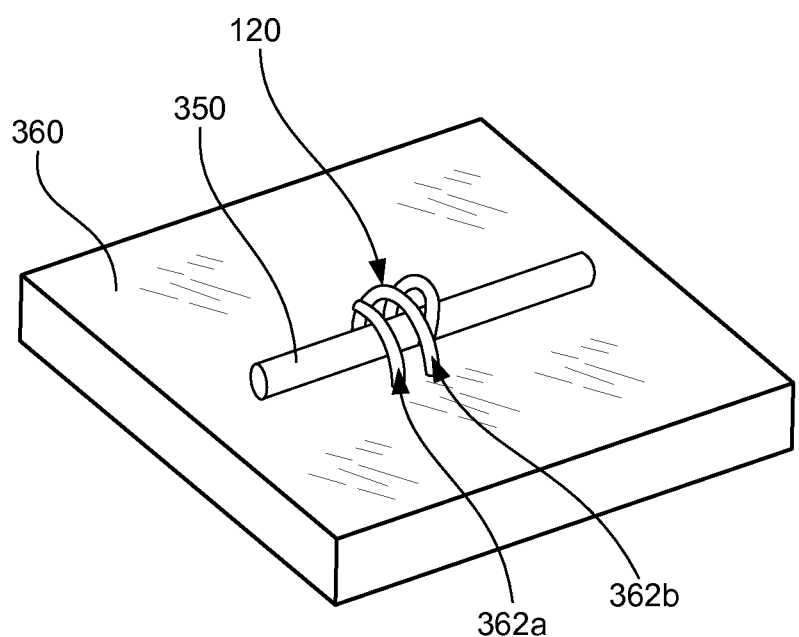
FIG. 3 is a perspective view of a fixation device according to an embodiment of the invention engaged with a bodily implant.

Referring to FIG. 3, a perspective view of a fixation device 120 engaged with a bodily implant is illustrated. In this illustrated embodiment, a single fixation device 120 is engaged with a bodily implant 350 to fasten the bodily implant to bodily tissue 360. The bodily implant 350 may be a single lead or wire or string that is fastened to the tissue 360 of a patient. The tissue 360 may be soft tissue or hard tissue.

The fixation device 120 has been inserted into the tissue 360 parallel to the plane of the tissue 360. As illustrated, the fixation device 120 fastens the bodily implant 350 at multiple fixation points 362*a* and 362*b*. In this manner, the fixation device 120 restricts all directions of movement of the bodily implant 350. The bodily implant 350 is restricted from moving away from the tissue 360 in horizontal and vertical directions. Said another way, the fixation device 120 secures the bodily implant 350 to the tissue 360 in multiple planes, which includes multiple directions.

As illustrated, the fixation device 120 is inserted into the tissue 360 to a specified depth and at a specified angle. In this example, the specified depth is less than the outside diameter of the fixation device 120. Said another way, the specified depth is no greater than the outside diameter of the fixation device 120 because at least a portion of the outside diameter of the fixation device 120 remains outside of the bodily tissue 360. In this example, the specified angle is an angle that is parallel to the plane of the bodily implant 350 and the tissue 360.

Figure 4:
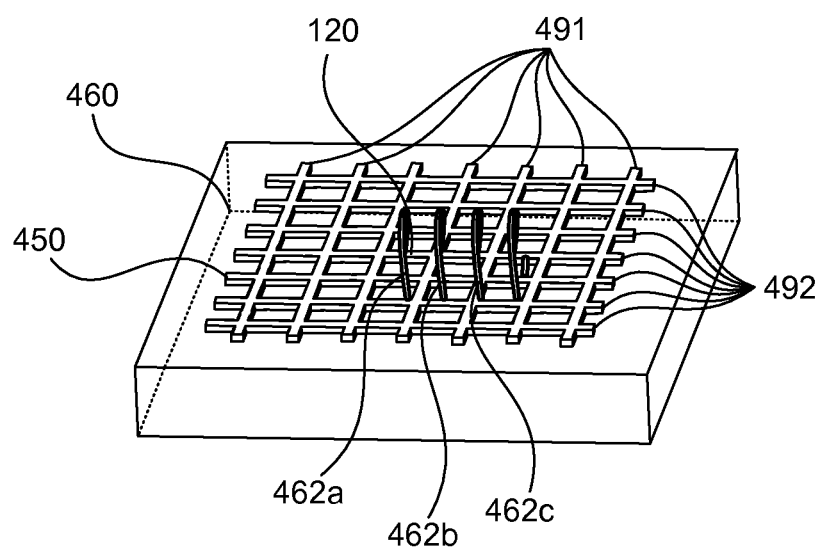
FIG. 4 is a perspective view of a fixation device according to an embodiment of the invention engaged with a bodily implant.

Referring to FIG. 4, a perspective view of a fixation device 120 engaged with a bodily implant is illustrated. In this illustrated embodiment, a single fixation device 120 is engaged with a bodily implant 450 to fasten the bodily implant to bodily tissue 460. The bodily implant 450 is a mesh, sheet or other implant suitable for treating tissue disorders. The mesh includes multiple vertical strands 491 and multiple horizontal strands 492 that form the mesh and define multiple mesh openings or mesh pores. The fixation device 120 may penetrate through a mesh opening and into the bodily tissue 460. The tissue 460 may be soft tissue or hard tissue.

The fixation device 120 has been inserted into the tissue 460 parallel to the plane of the tissue 460. As illustrated, the fixation device 120 fastens the bodily implant 450 at multiple fixation points 462*a*-462*c*. In this manner, the fixation device 120 restricts all directions of movement of the bodily implant 450. The bodily implant 450 is restricted from moving away from the tissue 460 in horizontal and vertical directions. Said another way, the fixation device 120 secures the bodily implant 450 to the tissue 460 in multiple planes, which includes multiple directions. The fixation device 120 spans across multiple mesh pores in both the horizontal and vertical directions. The fixation device 120 extends through more than one mesh pore. For example, the fixation device 120 extends through multiple mesh pores in both the horizontal and vertical directions. A single turn of the coil of the fixation device 120 may extend through multiple mesh pores. The single turn of the coil may extend through one mesh pore and through an adjacent mesh pore. The single turn of the coil may extend through one mesh pore, across an adjacent mesh pore and through another mesh pore. Multiple turns of the coils may extend through multiple adjacent and/or non-adjacent mesh pores.

As illustrated, a diameter of the fixation device 120 is larger than at least one of the mesh pores. In this manner, one turn of the fixation device 120 may span across at least two vertical strands 491 and may span across at least two horizontal strands 492.

As illustrated, the fixation device 120 is inserted into the tissue 460 to a specified depth and at a specified angle. In this example, the specified depth is less than the outside diameter of the fixation device 120. Said another way, the specified depth is no greater than the outside diameter of the fixation device 120 because at least a portion of the outside diameter of the fixation device 120 remains outside of the bodily tissue 460. In this example, the specified angle is an angle that is parallel to the plane of the bodily implant 450 and the tissue 460.

Figure 5:
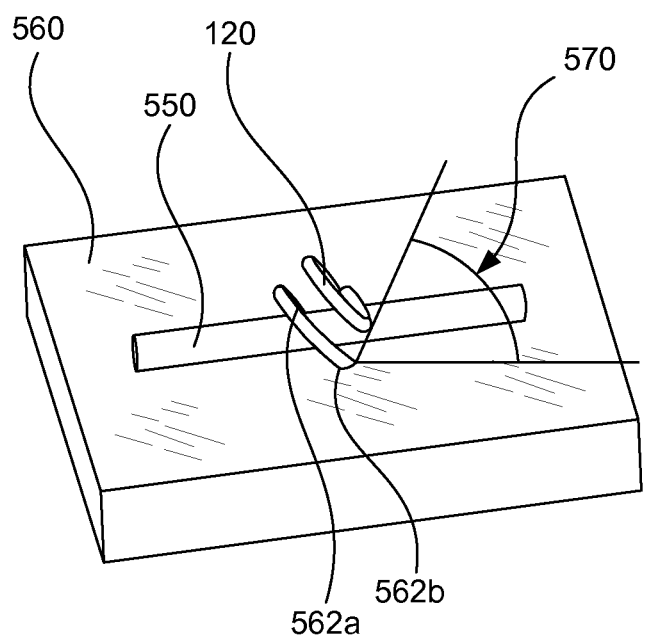
FIG. 5 is a perspective view of a fixation device according to an embodiment of the invention engaged with a bodily implant.

Referring to FIG. 5, a perspective view of a fixation device 120 engaged with a bodily implant is illustrated. In this illustrated embodiment, a single fixation device 120 is engaged with a bodily implant 550 to fasten the bodily implant to bodily tissue 560. The bodily implant 550 may be a single lead or wire or string that is fastened to the tissue 560 of a patient. The tissue 560 may be soft tissue or hard tissue.

The fixation device 120 has been inserted into the tissue 560 at an angle 570 to the plane of the tissue 560. As illustrated, the fixation device 120 fastens the bodily implant 550 at multiple fixation points 562*a* and 562*b*. In this manner, the fixation device 120 restricts all directions of movement of the bodily implant 550. The bodily implant 550 is restricted from moving away from the tissue 560 in horizontal and vertical directions. Said another way, the fixation device 120 secures the bodily implant 550 to the tissue 560 in multiple planes, which includes multiple directions.

As illustrated, the fixation device 120 is inserted into the tissue 560 to a specified depth and at a specified angle. In this example, the specified depth is less than the length of the fixation device 120. Said another way, the specified depth is no greater than the length of the fixation device 120 because at least a portion of the fixation device 120 remains outside of the bodily tissue 560. In this example, the specified angle is at an angle 570 (such as a non-parallel angle) to the plane of the bodily implant 550 and the tissue 560. The angle of insertion of fixation device 120 may be influenced by the angle of opening 136, by the angle of the delivery device during the procedure, by preforming the fixation device to bend at an angle once it exits opening 136 or by any combination of the above.

Figure 6:
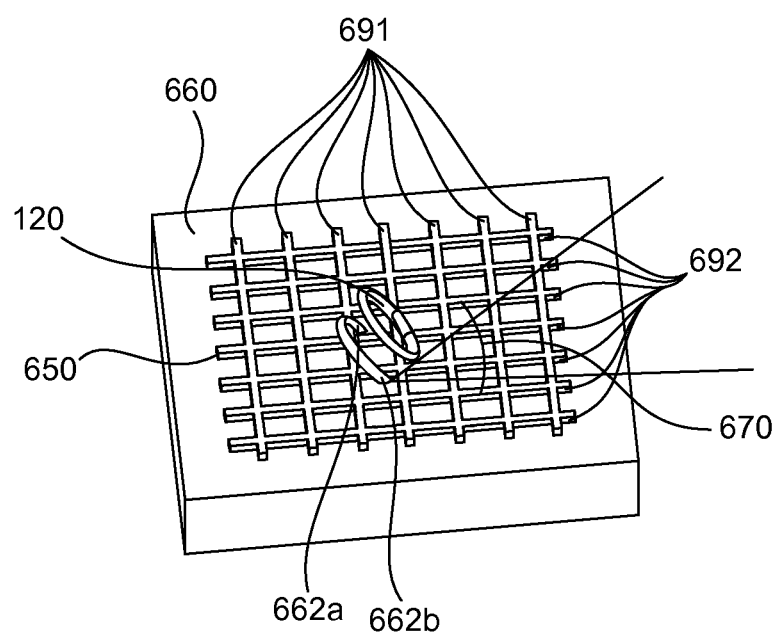
FIG. 6 is a perspective view of a fixation device according to an embodiment of the invention engaged with a bodily implant.

Referring to FIG. 6, a perspective view of a fixation device 120 engaged with a bodily implant is illustrated. In this illustrated embodiment, a single fixation device 120 is engaged with a bodily implant 650 to fasten the bodily implant to bodily tissue 660. The bodily implant 650 is a mesh, sheet or other implant suitable for treating tissue disorders. The mesh may include multiple vertical strands 691 and multiple horizontal strands 692 that form the mesh and define multiple mesh openings or mesh pores. A mesh can be woven, braided or twisted with may different angles or patterns. The mesh also may be a sheet of material. The fixation device 120 may penetrate through a mesh opening and into the bodily tissue 660. The tissue 660 may be soft tissue or hard tissue.

The fixation device 120 has been inserted into the tissue 660 at an angle 670 to the plane of the tissue 660. As illustrated, the fixation device 120 fastens the bodily implant 650 at multiple fixation points 662a and 662b. In this manner, the fixation device 120 restricts all directions of movement of the bodily implant 650. The bodily implant 650 is restricted from moving away from the tissue 660 in horizontal and vertical directions. Said another way, the fixation device 120 secures the bodily implant 650 to the tissue 660 in multiple planes, which includes multiple directions. The fixation device 120 spans across multiple mesh pores in both the horizontal and vertical directions. The fixation device 120 extends through more than one mesh pore. For example, the fixation device 120 extends through multiple mesh pores in both the horizontal and vertical directions. A single turn of the coil of the fixation device 120 may extend through multiple mesh pores. The single turn of the coil may extend through one mesh pore and through an adjacent mesh pore. The single turn of the coil may extend through one mesh pore, across an adjacent mesh pore and through another mesh pore. Multiple turns of the coils may extend through multiple adjacent and/or non-adjacent mesh pores.

As illustrated, a diameter of the fixation device 120 is larger than at least one of the mesh pores. In this manner, one turn of the fixation device 120 may span across at least two vertical strands 691 and may span across at least two horizontal strands 692.

As illustrated, the fixation device 120 is inserted into the tissue 660 to a specified depth and at a specified angle. In this example, the specified depth is less than the length of the fixation device 120. Said another way, the specified depth is no greater than the length of the fixation device 120 because at least a portion of the fixation device 120 remains outside of the bodily tissue 660. In this example, the specified angle is an angle 670 (such as a non-parallel angle) to the plane of the bodily implant 650 and the tissue 660.

Figure 7:
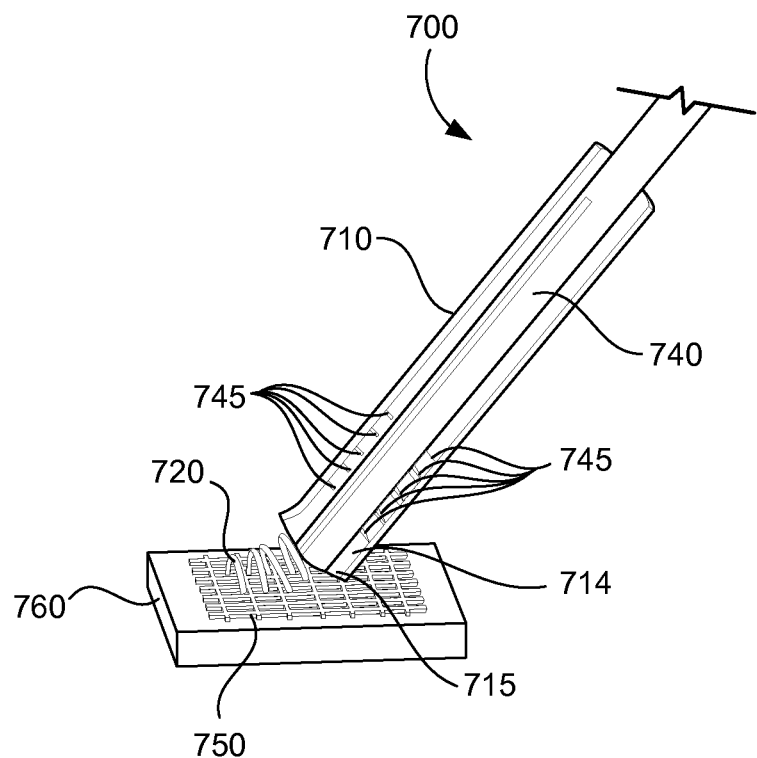
FIG. 7 is a perspective view of a medical device, including a partial breakaway view, and a fixation device according to an embodiment of the invention.

FIG. 7 is a perspective view, including a partial break away side view, of an apparatus 700 engaged with a bodily implant 750. The apparatus 700 may include some or all of the features of the apparatus 100 described above with respect to FIG. 1. The apparatus 700 includes an elongate member 710, a fixation device 720 and a driving member 740.

The apparatus 700 is configured to be inserted into a body of a patient such that at least a portion of the apparatus 700 is disposed within the body of the patient. As will be discussed in more detail below, the apparatus is configured to be placed adjacent a desired coupling or fixation location within the body.

The apparatus 700 is configured to insert the fixation device 720 into bodily tissue 760 to secure bodily implant 750 to the tissue 760. The apparatus 700 is configured to deliver the fixation device 720 at a desired angle into the bodily tissue 760 to control the depth of penetration of the fixation device 720.

The elongate member 710 includes a distal end 714. In the illustrated embodiment, the distal end 714 is angled or beveled to a desired angle to deliver the fixation device 720 at a particular angle. For example, the distal end 714 may include a bent or angled portion 715. Said another way, the distal end 714, which includes a tip of the elongate member 710, may be bent or angled from the rest of the elongate member 710. In this manner, the angled portion at the distal end 714 of the elongate member 710 is configured to drive or insert the fixation device 720 at an angle to the bodily implant 750 and to the tissue 760. In this example, the distal end 714 is bent to guide the fixation device 720 in a horizontal manner, which is in a plane parallel to the tissue 760 and to the bodily implant 750. The angle of insertion of fixation device 720 may be influenced by the angle of the opening, by the angle of the delivery device during the procedure, by preforming the fixation device to bend at an angle once it exits the opening or by any combination of the above.

In the illustrated embodiment, the angled portion 715 may be angled relative to a body portion of the elongate member 710. In some example embodiments, the angled portion 715 may be configured at a fixed angle. For example, in one embodiment, the angled portion 715 may be angled at a 45 degree angle with respect to the body portion of the elongate member 710. In other embodiments, the angled portion 715 may be fixed at other angles within the range of slightly more than 0 degrees to 90 degrees. In this manner, the angled portion 715 may guide the fixation device 720 into the bodily tissue 760 at a pre-determined fixed angle.

In other example embodiments, the angled portion 715 may be configured as an adjustable angle. For example, the angled portion 715 may be flexible to enable the angled portion 715 to be set at one of multiple different angles with respect to a body portion of the elongate member 710. The multiple different angles may include angles in the range of 0 degrees to 90 degrees. In this manner, a user of the apparatus 700 may set the angled portion 715 to a desired angle for delivery of the fixation device 720 at the desired angle.

In the illustrated embodiment, the apparatus 700 includes multiple guide members 745. The guide members 745 may be arranged around an inner surface of the elongate member 710. The guide members 745 may be arranged around the inner surface of the elongate member 710 for a portion of the length of the elongate member 710. In the illustrated example, the guide members 745 may be arranged near or at the distal end 714 of the elongate member 710.

The guide members 745 may be configured as threads to guide the fixation device 720 from a position inside the elongate member 710 to a location outside of the elongate member 710 at an angle related to the angle portion 715.

The fixation device 720 extends through more than one mesh pore of the bodily implant 750. For example, the fixation device 720 extends through multiple mesh pores in both the horizontal and vertical directions. A single turn of the coil of the fixation device 720 may extend through multiple mesh pores. The single turn of the coil may extend through one mesh pore and through an adjacent mesh pore. The single turn of the coil may extend through one mesh pore, across an adjacent mesh pore and through another mesh pore. Multiple turns of the coils may extend through multiple adjacent and/or non-adjacent mesh pores. A ratio of delivery turns to coil turns may be designed into the delivery device, for example, to assist in preventing too many turns of the fixation device. For example, the pusher may have a mechanism (e.g., gears) that only permit one coil turn in response to multiple pusher turns.

Figure 8:
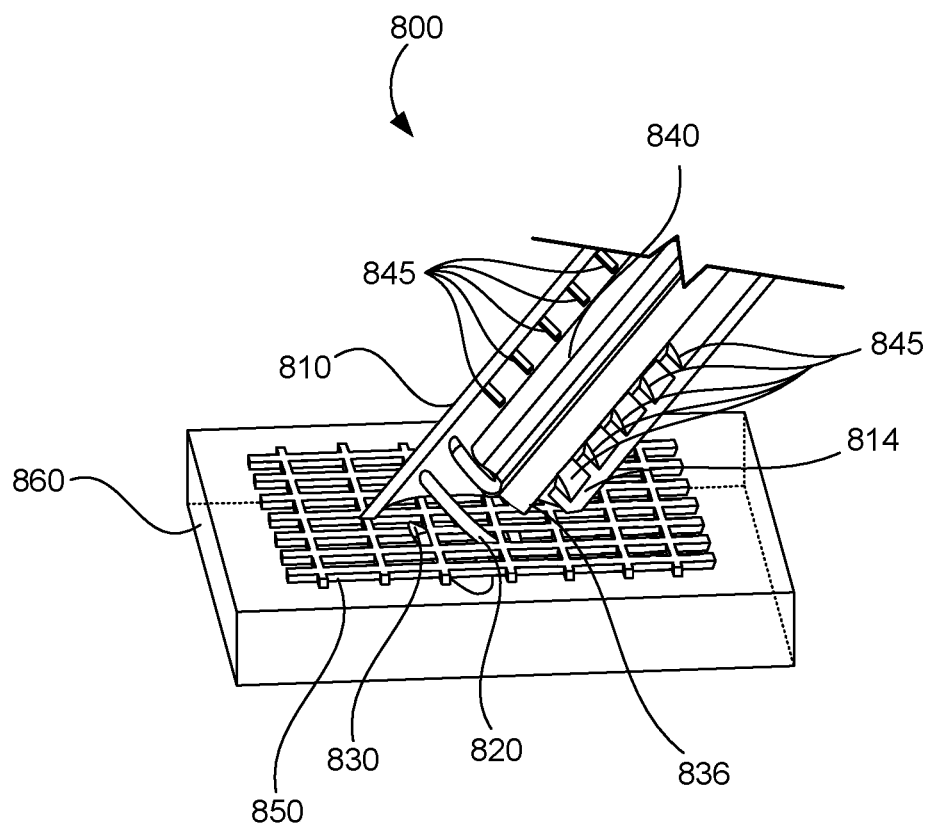
FIG. 8 is a perspective view of a medical device, including a partial breakaway view, and a fixation device according to an embodiment of the invention.

FIG. 8 is a perspective view, including a partial break away side view, of an apparatus 800 engaged with a bodily implant 850. The apparatus 800 may include some or all of the features of the apparatus 100 described above with respect to FIG. 1. The apparatus 800 includes an elongate member 810, a fixation device 820 having a tissue piercing portion 830, and a driving member 840.

The apparatus 800 is configured to be inserted into a body of a patient such that at least a portion of the apparatus 800 is disposed within the body of the patient. As will be discussed in more detail below, the apparatus is configured to be placed adjacent a desired coupling or fixation location within the body.

The apparatus 800 is configured to insert the fixation device 820 into bodily tissue 860 to secure bodily implant 850 to the tissue 860. The apparatus 800 is configured to deliver the fixation device 820 at a desired angle into the bodily tissue 860 to control the depth of penetration of the fixation device 820.

The elongate member 810 includes a distal end 814. In the illustrated embodiment, the distal end 814 includes an opening 836 that is angled or beveled to a desired angle to deliver the fixation device 820 at a particular angle. In this manner, the angled opening 836 at the distal end 814 of the elongate member 810 is configured to drive or insert the fixation device 820 at an angle to the bodily implant 850 and to the tissue 860. In this example, the opening 836 at the distal end 814 is angled to guide the fixation device 820 at an oblique angle to the plane of the tissue 860 and of the bodily implant 850.

In some example embodiments, the angled opening 836 may be configured at a fixed angle. In this manner, the angled opening 836 may guide the fixation device 820 into the bodily tissue 860 at a pre-determined fixed angle.

In other example embodiments, the angled opening 836 may be configured as an adjustable angle. For example, the angled opening 836 may be adjustable to enable the angled opening 836 to be set at one of multiple different angles. In this manner, a user of the apparatus 800 may set the angled opening 836 to a desired angle for delivery of the fixation device 820 at the desired angle. For instance, a portion of the elongate member 810 may be retracted or extended to change the angle of the opening 836. In another embodiment, the tip of the fixation device 820 may be formed to malleable (shape memory) material to a desired angle.

In the illustrated embodiment, the apparatus 800 includes multiple guide members 845. The guide members 845 may be arranged around an inner surface of the elongate member 810. The guide members 845 may be arranged around the inner surface of the elongate member 810 for a portion of the length of the elongate member 810. In the illustrated example, the guide members 845 may be arranged near or at the distal end 814 of the elongate member 810.

The guide members 845 may be configured as threads to guide the fixation device 820 from a position inside the elongate member 810 to a location outside of the elongate member 810 at an angle related to the angled opening 836.

The fixation device 820 extends through more than one mesh pore of the bodily implant 850. For example, the fixation device 820 extends through multiple mesh pores in both the horizontal and vertical directions. A single turn of the coil of the fixation device 820 may extend through multiple mesh pores. The single turn of the coil may extend through one mesh pore and through an adjacent mesh pore. The single turn of the coil may extend through one mesh pore, across an adjacent mesh pore and through another mesh pore. Multiple turns of the coils may extend through multiple adjacent and/or non-adjacent mesh pores.

Figure 9:
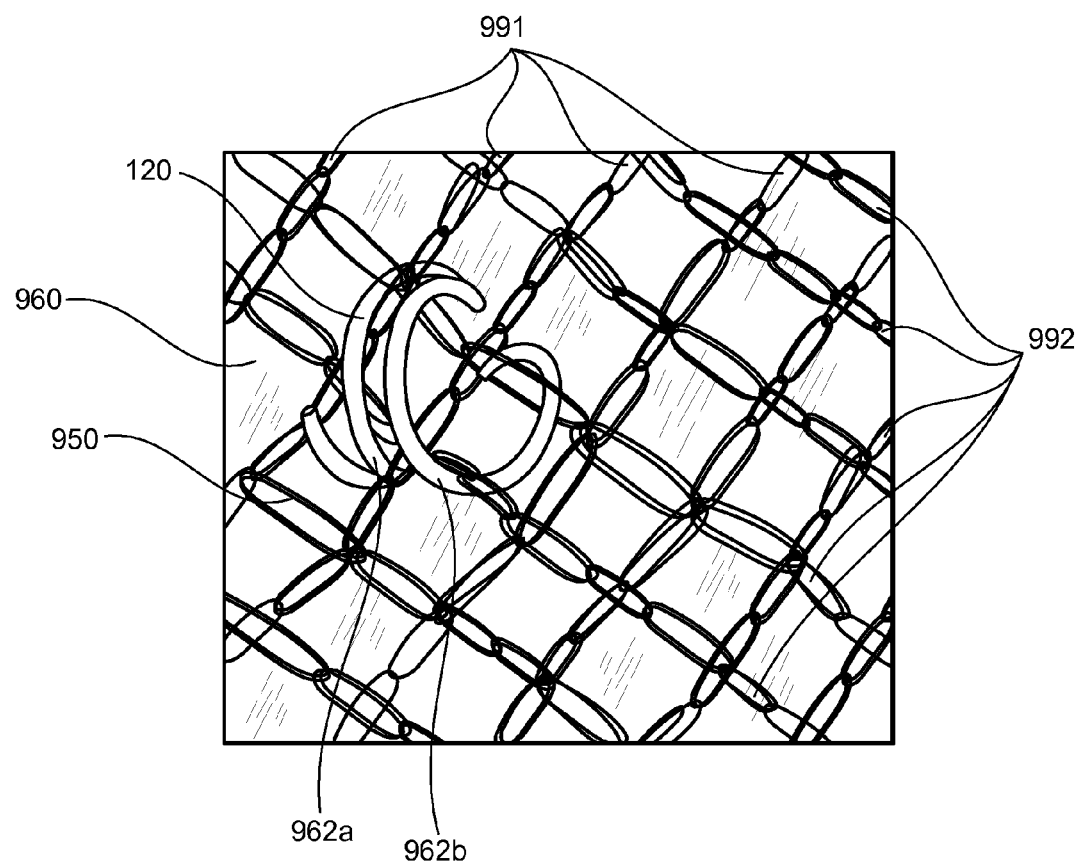
FIG. 9 is a perspective view of a fixation device according to an embodiment of the invention engaged with a bodily implant.
Figure 10:
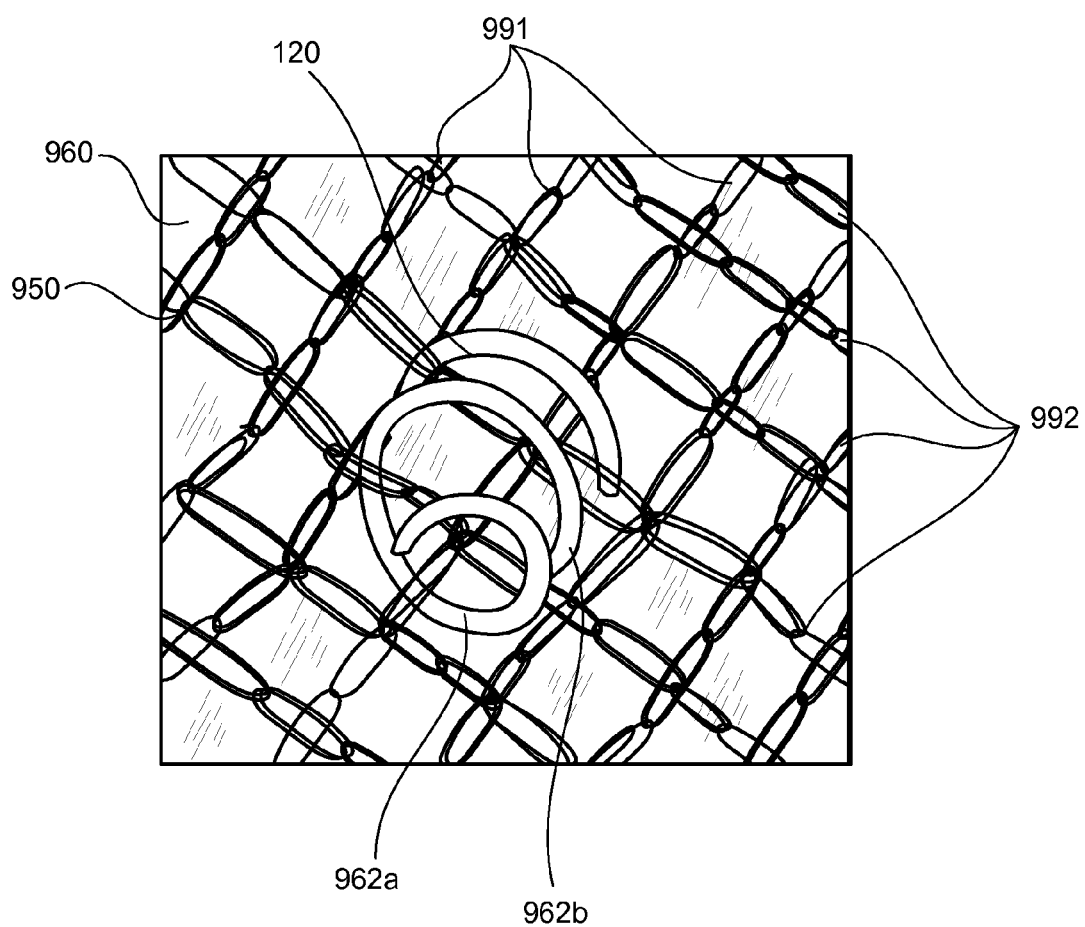
FIG. 10 is a perspective view of a fixation device according to an embodiment of the invention engaged with a bodily implant.
Figure 11:
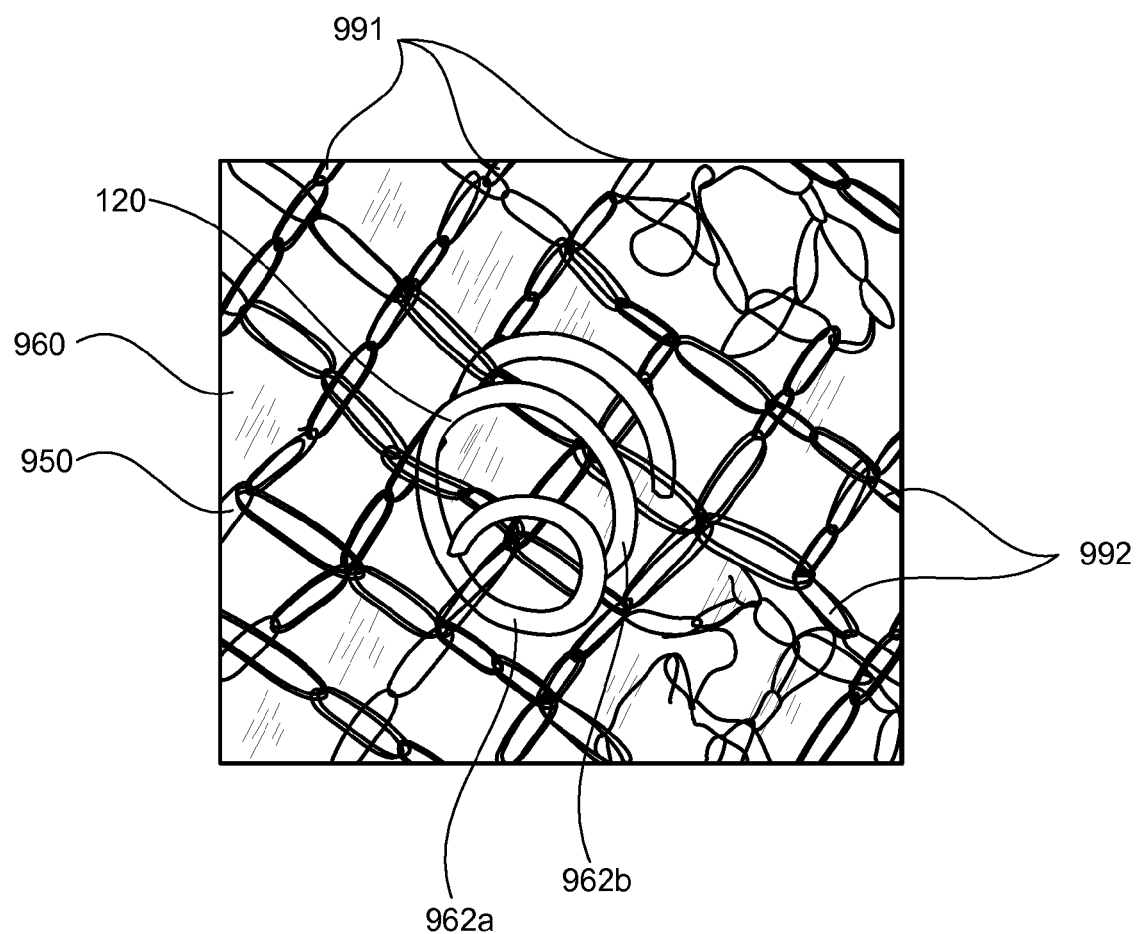
FIG. 11 is a perspective view of a fixation device according to an embodiment of the invention engaged with a bodily implant.

Referring to FIGS. 9, 10 and 11, perspective views of a fixation device 120 engaged with a bodily implant are illustrated. In these illustrated embodiments, a single fixation device 120 is engaged with a bodily implant 950 to fasten the bodily implant to bodily tissue 960, with the fixation device 120 being illustrated in different deployments (or insertions) in each of the various example FIGS. 9-11. The bodily implant 950 is a mesh, sheet or other implant suitable for treating tissue disorders. The mesh includes multiple vertical strands 991 and multiple horizontal strands 992 that form the mesh and define multiple mesh openings or mesh pores. The fixation device 120 may penetrate through a mesh opening and into the bodily tissue 960. The tissue 960 may be soft tissue or hard tissue.

The fixation device 120 has been inserted into the tissue 960 at an angle to the plane of the tissue 960. As illustrated, the fixation device 120 fastens the bodily implant 950 at multiple fixation points 962a and 962b. In this manner, the fixation device 120 restricts all directions of movement of the bodily implant 950. The bodily implant 950 is restricted from moving away from the tissue 960 in horizontal and vertical directions. Said another way, the fixation device 120 secures the bodily implant 950 to the tissue 960 in multiple planes, which includes multiple directions. The fixation device 120 spans across multiple mesh pores in both the horizontal and vertical directions.

As illustrated, a diameter of the fixation device 120 is larger than at least one of the mesh pores. In this manner, one turn of the fixation device 120 may span across at least two vertical strands 991 and may span across at least two horizontal strands 992. The fixation device 120 extends through more than one mesh pore. For example, the fixation device 120 extends through multiple mesh pores in both the horizontal and vertical directions. A single turn of the coil of the fixation device 120 may extend through multiple mesh pores. The single turn of the coil may extend through one mesh pore and through an adjacent mesh pore. The single turn of the coil may extend through one mesh pore, across an adjacent mesh pore and through another mesh pore. Multiple turns of the coils may extend through multiple adjacent and/or non-adjacent mesh pores.

As illustrated, the fixation device 120 is inserted into the tissue 960 to a specified depth and at a specified angle. In these examples, the specified depth is less than the diameter of the fixation device 120. Said another way, the specified depth is no greater than the diameter of the fixation device 120 because at least a portion of the fixation device 120 remains outside of the bodily tissue 960. In these examples, the specified angle may be in a plane parallel to the plane of the bodily implant 950 and the tissue 960.

Figure 12:
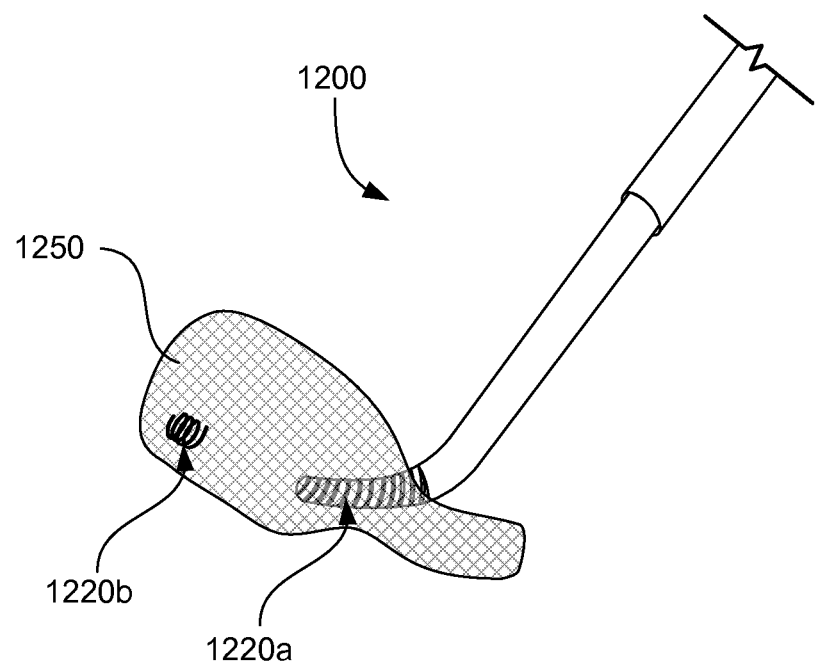
FIG. 12 is a schematic illustration of an apparatus and a fixation device according to an embodiment of the invention.

FIG. 12 is a schematic illustration of an apparatus 1200 according to an example embodiment. The apparatus 1200 may include some or all of the features of the apparatus 100 described above with respect to FIG. 1. The apparatus 1200 includes a single continuous coil-shaped fastener 1220a that may be cut into multiple coil-shaped fasteners such as coil-shaped fastener 1220b.

The apparatus 1200 is configured to be inserted into a body of a patient such that at least a portion of the apparatus 1200 is disposed within the body of the patient. As will be discussed in more detail below, the apparatus is configured to be placed adjacent a desired coupling or fixation location within the body.

The apparatus 1200 is configured to insert the coil-shaped fastener 1220a into bodily tissue to secure bodily implant 1250 to the tissue. The apparatus 1200 is configured to cut the coil-shaped fastener 1220a into multiple fasteners (e.g., fastener 1220b) that can be inserted into the tissue. The apparatus 1200 is configured to deliver the coil-shaped fastener 1220a at a desired angle into the bodily tissue to control the depth of penetration of the fastener 1220a. As discussed above with respect to FIG. 1, in some example embodiments, the apparatus 1200 may include a cutting member (not shown) or may use an external cutting implement to cut the continuous coil 1220a into single fasteners 1220b.

Figure 13:
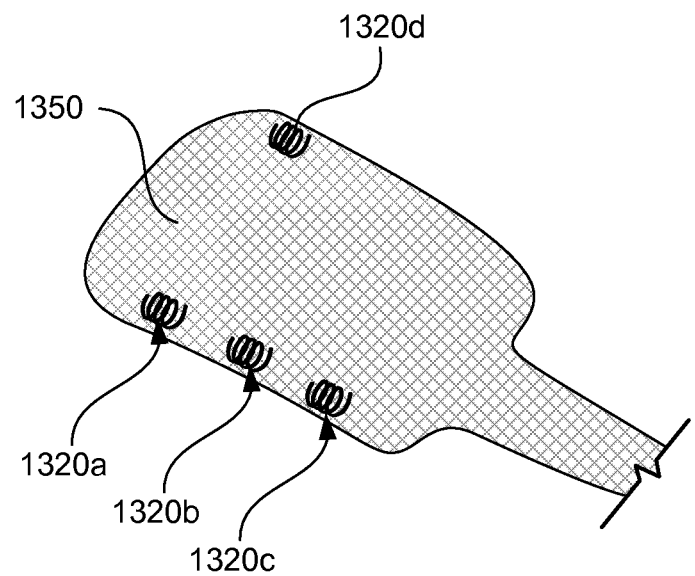
FIG. 13 is a schematic illustration of a fixation device according to an embodiment of the invention engaged with a bodily implant.

FIG. 13 is a schematic illustration of multiple coil-shaped fasteners 1320a-1320d securing a bodily implant 1350 to tissue. The coil-shaped fasteners 1320a-1320d may include the same or similar features described above with respect to the fixation device 120 of FIG. 1.

In this illustrated embodiment, the coil-shaped fasteners 1320a-1320d are illustrated as securing an outer edge of the bodily implant 1350 to the tissue.

Figure 14:
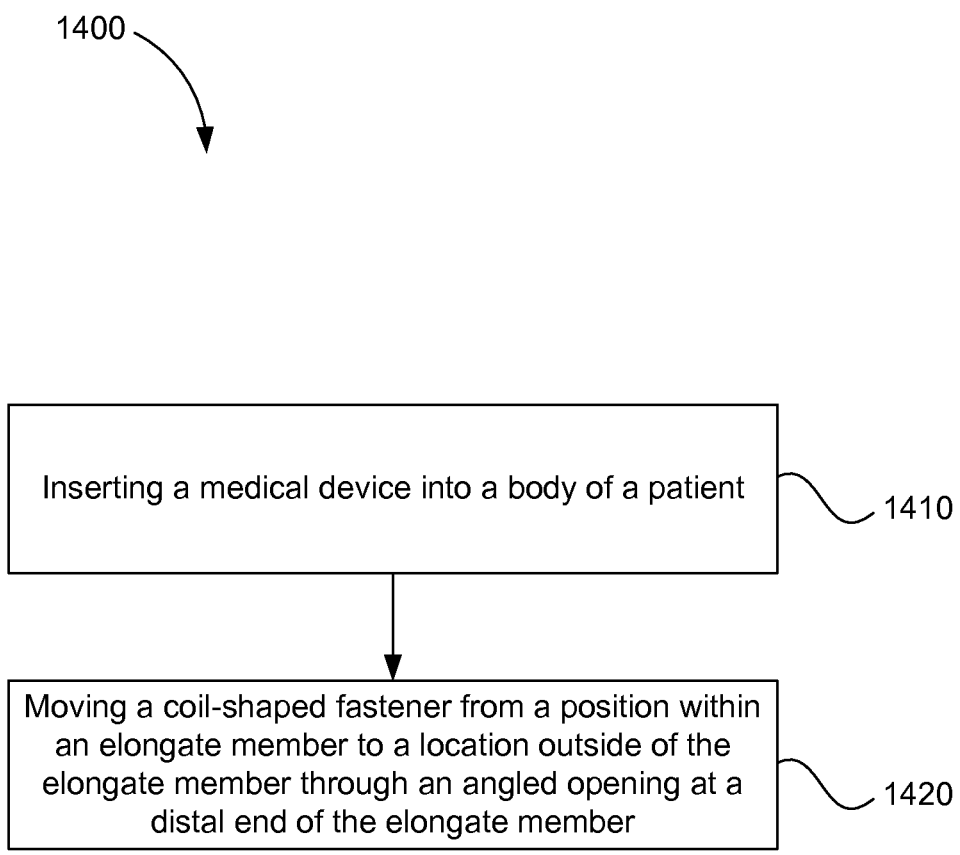
FIG. 14 is a flow chart of a method of placing an implant within a body of a patient according to an embodiment of the invention.

FIG. 14 is a flow chart of a method 1400 of placing a coil-shaped fastener within bodily tissue according to an embodiment of the invention. At 1410, a medical device is inserted into a body of the patient. In some embodiments, the medical device includes an elongate member defining a lumen, a coil-shaped fastener disposed at least partially in the elongate member and a driving member. The elongate member includes an angled opening at a distal end of the elongate member. At 1420, the coil-shaped fastener is moved from a position within the elongate member to a location outside of the cartridge through the angled opening. As the coil-shaped fastener is moved through the angled opening, the coil-shaped fastener is angled and enters the bodily tissue at an angle. The fastener angle may be defined by the angle of the opening at the distal end of the elongate member.

The medical device may deliver the coil-shaped fastener to a fixed penetration depth, as may be defined by a diameter or a length of the coil-shaped fastener and the angle in which the fastener is inserted by the medical device. In this manner, as the fastener enters the bodily tissue, the fastener penetrates to a fixed depth and may be prevented from penetrating deeper into the tissue. In one example, the method and medical device may be used to secure a bodily implant (e.g., a mesh having mesh pores) to bodily tissue. The medical device may cause the fastener to pierce through the mesh pores and the bodily tissue to a defined penetration depth and to secure the mesh against the bodily tissue. In this manner, one part of the fastener may be on one side of the mesh penetrating into the bodily tissue and another part of the fastener may be on the opposite side of the mesh holding the mesh against the bodily tissue. The fastener may extend through more than one mesh pore. For example, the fastener extends through multiple mesh pores in both the horizontal and vertical directions. A single turn of the coil of the fastener may extend through multiple mesh pores. The single turn of the coil may extend through one mesh pore and through an adjacent mesh pore. The single turn of the coil may extend through one mesh pore, across an adjacent mesh pore and through another mesh pore. Multiple turns of the coils may extend through multiple adjacent and/or non-adjacent mesh pores.

In some embodiments, the medical device may be used to insert fixation devices into bodily tissue to secure one bodily tissue with another bodily tissue. The medical device and fixation device may be configured to function in the manner described above with respect to fastening a bodily implant to bodily tissue, except that the devices are being used to fasten bodily tissue to bodily tissue.

In one embodiment, a medical device includes an elongate member, a fixation device and a driving member. The elongate member defines a lumen and includes a proximal end and a distal end. The distal end of the elongate member has an opening. The fixation device is at least partially disposed within the elongate member and includes a tissue piercing portion at a distal end of the fixation device. The driving member is at least partially disposed within the elongate member and is configured to move the fixation device from a position within the lumen to a location outside of the lumen through the opening. The opening at the distal end of the elongate member is angled to insert the fixation device in a tissue of a patient at an angle to a plane of the tissue of the patient to fasten a bodily implant to the tissue.

In some embodiments, the fixation device is a coil-shaped fastener.

In some embodiments, the opening at the distal end of the elongate member is angled to insert the fixation device in the tissue of the patient parallel to the plane of the tissue of the patient to fasten the bodily implant to the tissue.

In some embodiments, the opening at the distal end of the elongate member is angled to insert the fixation device in the tissue of the patient at an oblique angle to the plane of the tissue of the patient to fasten the bodily implant to the tissue.

In some embodiments, the angle of the opening at the distal end of the elongate member is fixed to insert the fixation device in the tissue of the patient at an angle corresponding to the fixed angle of the distal end of the elongate member relative to the tissue.

In some embodiments, the angle of the opening at the distal end of the elongate member is adjustable to insert the fixation device in the tissue of the patient at an angle corresponding to the adjustable angle of the distal end of the elongate member.

In some embodiments, the fixation device is delivered to fasten the bodily implant to the tissue at multiple points of fixation in multiple different planes.

In some embodiments, the bodily implant is a mesh implant having multiple strands and the fixation device fastens the mesh implant to the tissue in multiple different planes.

In some embodiments, the fixation device is a coil-shaped fastener and the bodily implant is a mesh implant having openings defined by multiple strands and a diameter of the coil-shaped fastener is greater than at least one of the openings of the mesh implant.

In some embodiments, the medical device further includes a plurality of the fixation devices, the fixation devices each having a fixed length and being separately insertable into the tissue of the patient to fasten the bodily implant to the tissue.

In some embodiments, the fixation device is a single continuous coil that is configurable to be separated into a plurality of coil-shaped fasteners. The medical device further includes a cutting member that is configured to separate the single continuous coil into the plurality of coil-shaped fasteners.

In one embodiment, a medical device includes an elongate member, a coil-shaped fastener and a driving member. The elongate member defines a lumen and includes a proximal end and a distal end. The distal end has an angled portion and an opening. The coil-shaped fastener is at least partially disposed within the elongate member and the coil-shaped fastener has an outside diameter. The driving member is at least partially disposed within the elongate member. The driving member is configured to move the coil-shaped fastener from a position within the lumen to a location outside of the lumen through the angled portion and the opening at the distal end of the elongate member and to insert the coil-shaped fastener in a tissue of a patient to fasten a bodily implant to the tissue.

In some embodiments, the angled portion is set at a fixed angle.

In some embodiments, the angled portion is adjustable to one of multiple different angles.

In some embodiments, an angle of penetration of the coil-shaped fastener into the tissue corresponds to an angle of the angled portion relative to the tissue.

In some embodiments, the coil-shaped fastener is configured to be separated into multiple coil-shaped fasteners.

In some embodiments, a depth of penetration into the tissue is less than the outside diameter of the coil-shaped fastener.

In some embodiments, a depth of penetration into the tissue is related to the length of the coil-shaped fastener and an angle of the angled portion.

In one embodiment, a method of placing a coil-shaped fastener within a body of a patient includes 1) inserting a medical device within the body of the patient, the medical device includes an elongate member defining a lumen, the elongate member having a distal end and an angled opening at the distal end and 2) moving the coil-shaped fastener from a position within the elongate member to a location outside of the elongate member through the angled opening at the distal end.

In some embodiments, moving the coil-shaped fastener includes engaging the coil-shaped fastener with a driving member of the medical device.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
   an elongate member defining a lumen, the elongate member having a proximal end and a distal end, the proximal end defining an opening, the distal end defining a beveled tip, the beveled tip having a beveled opening, the lumen extending along a longitudinal axis of the elongate member between the opening and the beveled opening;
   a fixation device at least partially disposed within the elongate member, the fixation device having a tissue piercing portion at a distal end of the fixation device; and
   a driving member at least partially disposed within the elongate member, the driving member configured to move the fixation device from a position within the lumen to a location outside of the lumen through the beveled opening at the beveled tip of the elongate member,
   wherein the beveled tip of the elongate member is at an offset from the longitudinal axis of the elongate member and angled at a non-right angle with respect to the longitudinal axis of the elongate member, and in response to the fixation device being moved to the location outside the lumen, the fixation device is configured to be inserted into a tissue layer of a patient at an angle to a plane of the tissue layer of the patient to fasten a bodily implant to the tissue layer.

2. The medical device of claim 1, wherein the fixation device is a coil-shaped fastener.

3. The medical device of claim 1, further comprising a handle coupled to the driving member, the handle configured to move the driving member in a direction parallel to the longitudinal axis and to rotate about a longitudinal axis of the driving member.

4. The medical device of claim 1, wherein the elongate member includes a plurality of guide members disposed around an inner surface of the elongate member proximate to the distal end, the plurality of guide members configured as threads to guide the fixation device from the position within the lumen to the location outside of the lumen.

5. The medical device of claim 1, wherein the angle of the beveled tip of the elongate member is fixed.

6. The medical device of claim 1, wherein the angle of the beveled tip of the elongate member is adjustable.

7. The medical device of claim 1, wherein the fixation device is delivered to fasten the bodily implant to the tissue layer at multiple points of fixation in multiple different planes.

8. The medical device of claim 1, wherein the bodily implant is a mesh implant having multiple strands and the fixation device fastens the mesh implant to the tissue layer in multiple different planes of the tissue layer.

9. The medical device of claim 1, wherein the fixation device is a coil-shaped fastener and the bodily implant is a mesh implant having openings defined by multiple strands and a diameter of the coil-shaped fastener is greater than at least one of the openings of the mesh implant.

10. The medical device of claim 1, further comprising a plurality of the fixation devices, the fixation devices each having a fixed length and being separately insertable into the tissue layer of the patient to fasten the bodily implant to the tissue layer.

11. The medical device of claim 1, wherein the fixation device is a single continuous coil that is configurable to be separated into a plurality of coil-shaped fasteners and further comprising a cutting member that is configured to separate the single continuous coil into the plurality of coil-shaped fasteners.

12. A medical device, comprising:
    an elongate member defining a lumen, the elongate member having a proximal end and a distal end, the proximal end defining an opening, the distal end defining a beveled tip, the beveled tip having a beveled opening, the lumen extending along a longitudinal axis of the elongate member between the opening and the beveled opening, the beveled tip of the elongate member being at an offset from the longitudinal axis of the elongate member and angled at a non-right angle with respect to the longitudinal axis of the elongate member;
    a coil-shaped fastener at least partially disposed within the elongate member, the coil-shaped fastener having a length and an outside diameter; and
    a driving member at least partially disposed within the elongate member, the driving member configured to move the coil-shaped fastener from a position within the lumen to a location outside of the lumen through the beveled opening at the beveled tip of the elongate member and to insert the coil-shaped fastener into a tissue layer of a patient to fasten a bodily implant to the tissue layer, the coil-shaped fastener is configured to be inserted into the tissue layer of the patient at an angle to a plane of the tissue layer of the patient.

13. The medical device of claim 12 wherein the angle of the beveled tip is set at a fixed angle.

14. The medical device of claim 12 wherein the angle of the beveled tip is adjustable to one of multiple different angles.

15. The medical device of claim 12 wherein an angle of penetration of the coil-shaped fastener into the tissue layer corresponds to the angle of the beveled tip relative to the plane of the tissue layer.

16. The medical device of claim 12 wherein the coil-shaped fastener is configured to be separated into multiple coil-shaped fasteners.

17. The medical device of claim 12 wherein a depth of penetration into the tissue is less than the outside diameter of the coil-shaped fastener.

18. The medical device of claim 12 wherein a depth of penetration into the tissue layer is related to the length of the coil-shaped fastener and the angle of the beveled tip relative to the plane of the tissue layer.

19. The medical device of claim 12, wherein the elongate member includes a plurality of guide members disposed around an inner surface of the elongate member proximate to the distal end, the plurality of guide members configured as threads to guide the coil-shaped fastener from the position within the lumen to the location outside of the lumen.

20. The medical device of claim 12, further comprising a handle coupled to the driving member, the handle configured to move the driving member in a direction parallel to the longitudinal axis and to rotate about a longitudinal axis of the driving member.

* * * * *